US012180206B2

(12) United States Patent
Horn

(10) Patent No.: US 12,180,206 B2
(45) Date of Patent: Dec. 31, 2024

(54) ACECLIDINE DERIVATIVES, COMPOSITIONS THEREOF AND METHODS OF USE THEREOF

(71) Applicant: LENZ Therapeutics Operations, Inc., Del Mar, CA (US)

(72) Inventor: Gerald Horn, Highland Park, IL (US)

(73) Assignee: LENZ THERAPEUTICS OPERATIONS, INC., Del Mar, CA (US)

( * ) Notice: Subject to any disclaimer, the term of this patent is extended or adjusted under 35 U.S.C. 154(b) by 0 days.

(21) Appl. No.: 17/988,366

(22) Filed: Nov. 16, 2022

(65) Prior Publication Data

US 2023/0151000 A1    May 18, 2023

Related U.S. Application Data

(60) Provisional application No. 63/280,228, filed on Nov. 17, 2021.

(51) Int. Cl.
| | | |
|---|---|---|
| *C07D 453/02* | (2006.01) | |
| *A61K 9/00* | (2006.01) | |
| *A61K 31/439* | (2006.01) | |
| *A61K 31/4748* | (2006.01) | |
| *A61K 47/40* | (2006.01) | |
| *A61P 27/02* | (2006.01) | |
| *A61P 27/06* | (2006.01) | |
| *C07D 471/00* | (2006.01) | |

(52) U.S. Cl.
CPC .......... *C07D 471/00* (2013.01); *A61K 9/0048* (2013.01); *A61K 31/4748* (2013.01); *A61K 47/40* (2013.01)

(58) Field of Classification Search
CPC .... C07D 453/02; A61K 31/439; A61K 47/40; A61P 27/02; A61P 27/06
See application file for complete search history.

(56) References Cited

U.S. PATENT DOCUMENTS

| | | |
|---|---|---|
| 4,474,751 A | 10/1984 | Haslam et al. |
| 4,906,467 A | 3/1990 | Schwartzman et al. |
| 5,073,560 A | 12/1991 | Wu et al. |
| 5,286,864 A | 2/1994 | Walther et al. |
| 5,451,587 A | 9/1995 | Walther et al. |
| 5,488,050 A | 1/1996 | Neufeld |
| 6,120,758 A | 9/2000 | Siddiqui et al. |
| 6,291,466 B1 | 9/2001 | Gwon et al. |
| 6,353,022 B1 | 3/2002 | Schneider et al. |
| 6,410,544 B1 | 6/2002 | Gwon et al. |
| 7,067,261 B2 | 6/2006 | Bencherif et al. |
| 8,299,079 B2 | 10/2012 | Kaufman |
| 8,455,494 B2 | 6/2013 | Kaufman |
| 8,501,800 B2 | 8/2013 | Bowman et al. |
| 8,524,758 B2 | 9/2013 | Benozzi |
| 9,089,562 B2 | 7/2015 | Horn et al. |
| 9,314,427 B2 | 4/2016 | Horn et al. |
| 9,320,709 B2 | 4/2016 | Horn et al. |
| 9,833,441 B2 | 12/2017 | Horn et al. |
| 9,844,537 B2 | 12/2017 | Horn et al. |
| 9,968,594 B2 | 5/2018 | Horn et al. |
| 10,052,313 B2 | 8/2018 | Horn et al. |
| 10,064,818 B2 | 9/2018 | Horn et al. |
| 10,307,408 B2 | 6/2019 | Horn et al. |
| 10,617,763 B2 | 4/2020 | Horn et al. |
| 10,836,760 B2 | 11/2020 | Horn |
| 10,959,990 B2 | 3/2021 | Horn |
| 11,179,327 B2 | 11/2021 | Horn et al. |
| 11,179,328 B2 | 11/2021 | Horn |
| 11,214,569 B2 | 1/2022 | Horn |
| 11,273,150 B2 | 3/2022 | Horn |
| 11,344,538 B2 | 5/2022 | Horn |
| 11,648,247 B1 | 5/2023 | Horn |
| 2002/0035264 A1 | 3/2002 | Kararli et al. |
| 2002/0036264 A1 | 3/2002 | Nakasuji et al. |
| 2003/0104996 A1 | 6/2003 | Li et al. |
| 2003/0140996 A1 | 7/2003 | Thomson |
| 2003/0165545 A1 | 9/2003 | Huth et al. |
| 2003/0232089 A1 | 12/2003 | Singh et al. |

(Continued)

FOREIGN PATENT DOCUMENTS

| | | |
|---|---|---|
| CN | 101262886 A | 9/2008 |
| CN | 101616640 A | 12/2009 |

(Continued)

OTHER PUBLICATIONS

CAS printout for Mashkovskii, The Relation Between the Chemical Structure and Pharmacological Activity of Some Esters of 3-Hydroxyquinuclidine (Quinuclidine-3-ol), Proc. Intern. Pharmacol., vol. 7, pp. 359-366 (Year: 1961).*
Primozic et al., Influence of the Acyl Moiety on the Hydrolysis of Quinuclidinium Esters Catalyzed by Butyrylcholinesterase, Croatica Chemica Acta, vol. 84, No. 2, pp. 245-249 (Year: 2011).*
Pubchem 427198483 deposited Aug. 13, 2020 p. 1-5.
International Search Report and the Written Opinion of the International Searching Authority in the corresponding PCT Application No. PCT/US022/050028 mailed Mar. 3, 2023.
AKORN Incorporated MSDS: Tropicacyl (R); Rev. 11-11 (date unknown).
Berge et al. Pharmaceutical Salts. Journal of Pharmaceutical Sciences 66(1):1-19 (Jan. 1977).
Bijsluiter: Glaucocare. Available at https://consumed.nl/bijsluiters/glaucocare. Machine Translation Provided. 2018.

(Continued)

*Primary Examiner* — Brenda L Coleman
(74) *Attorney, Agent, or Firm* — WILSON SONSINI GOODRICH & ROSATI

(57) ABSTRACT

The present invention is directed to derivatives of aceclidine. The present invention is further directed to ophthalmological compositions comprising a therapeutically effective amount of a compound of the present invention and one or more pharmaceutically acceptable excipients. The present invention is further directed to a methods of treating presbyopia or glaucoma or reducing hyperemia comprising administering to a patient in need thereof a therapeutically effective amount of a compound of the present invention.

6 Claims, No Drawings

(56) References Cited

U.S. PATENT DOCUMENTS

| | | |
|---|---|---|
| 2004/0106644 A1 | 6/2004 | Randazzo |
| 2004/0142829 A1 | 7/2004 | Tsao et al. |
| 2005/0196370 A1 | 9/2005 | Yu et al. |
| 2006/0172972 A1 | 8/2006 | Bhushan et al. |
| 2006/0177430 A1 | 8/2006 | Bhushan et al. |
| 2007/0297990 A1 | 12/2007 | Shah et al. |
| 2009/0074786 A1 | 3/2009 | Dor et al. |
| 2009/0156581 A1 | 6/2009 | Dillon et al. |
| 2009/0297565 A1 | 12/2009 | Müller et al. |
| 2009/0297566 A1 | 12/2009 | Brinkman et al. |
| 2010/0016395 A1 | 1/2010 | Benozzi |
| 2010/0310476 A1 | 12/2010 | Tamarkin et al. |
| 2011/0172302 A1 | 7/2011 | Dalton et al. |
| 2011/0250294 A1 | 10/2011 | Tien et al. |
| 2011/0251285 A1 | 10/2011 | Tien et al. |
| 2012/0028910 A1 | 2/2012 | Combal et al. |
| 2012/0094962 A1 | 4/2012 | Skulachev |
| 2012/0165295 A1 | 6/2012 | Painter et al. |
| 2012/0315265 A1 | 12/2012 | Lai et al. |
| 2013/0245030 A1 | 9/2013 | Kaufman |
| 2014/0113946 A1 | 4/2014 | Abad |
| 2014/0221446 A1 | 8/2014 | Meyer |
| 2014/0378401 A1 | 12/2014 | Horn |
| 2015/0010634 A1 | 1/2015 | Knappe et al. |
| 2015/0065511 A1 | 3/2015 | Horn et al. |
| 2015/0290125 A1 | 10/2015 | Horn et al. |
| 2015/0290126 A1 | 10/2015 | Horn et al. |
| 2015/0290216 A1 | 10/2015 | Khopade et al. |
| 2016/0008278 A1 | 1/2016 | Horn et al. |
| 2016/0008337 A1 | 1/2016 | Horn et al. |
| 2016/0018671 A1 | 1/2016 | Waite et al. |
| 2016/0193193 A1 | 7/2016 | Horn et al. |
| 2016/0193194 A1 | 7/2016 | Horn et al. |
| 2016/0346259 A1 | 12/2016 | Horn et al. |
| 2016/0354315 A1 | 12/2016 | Li |
| 2018/0140708 A1 | 5/2018 | Horn et al. |
| 2018/0228729 A1 | 8/2018 | Lee et al. |
| 2018/0235946 A1 | 8/2018 | Horn et al. |
| 2018/0280363 A1 | 10/2018 | Horn et al. |
| 2019/0000755 A1 | 1/2019 | Horn et al. |
| 2019/0038609 A1 | 2/2019 | Horn |
| 2019/0240152 A1 | 8/2019 | Horn et al. |
| 2019/0321337 A1 | 10/2019 | Robinson et al. |
| 2020/0115377 A1 | 4/2020 | Horn |
| 2020/0146976 A1 | 5/2020 | Horn |
| 2020/0181136 A1 | 6/2020 | Horn |
| 2020/0188369 A1 | 6/2020 | Horn |
| 2020/0281906 A1 | 9/2020 | Horn |
| 2020/0308168 A1 | 10/2020 | Banerjee et al. |
| 2021/0038574 A1 | 2/2021 | Horn |
| 2021/0251970 A1 | 8/2021 | Horn |
| 2022/0031608 A1 | 2/2022 | Horn |
| 2022/0105090 A1 | 4/2022 | Horn |
| 2022/0233434 A1 | 7/2022 | Horn |
| 2022/0347170 A1 | 11/2022 | Horn |
| 2023/0190738 A1 | 6/2023 | Horn |
| 2023/0190739 A1 | 6/2023 | Horn |
| 2023/0248644 A1 | 8/2023 | Horn |
| 2023/0310392 A1 | 10/2023 | Horn |
| 2023/0398064 A1 | 12/2023 | Horn |
| 2023/0398113 A1 | 12/2023 | Horn |
| 2023/0404912 A1 | 12/2023 | Horn |
| 2023/0414494 A1 | 12/2023 | Horn |
| 2023/0414587 A1 | 12/2023 | Horn |
| 2024/0091207 A1 | 3/2024 | Horn |

FOREIGN PATENT DOCUMENTS

| | | |
|---|---|---|
| EP | 0197718 A2 | 10/1986 |
| JP | S62194861 A | 8/1987 |
| JP | H06211666 A | 8/1994 |
| JP | H07330604 A | 12/1995 |
| JP | 2852607 B2 | 2/1999 |
| JP | H11292151 A | 10/1999 |
| JP | 2002521429 A | 7/2002 |
| JP | 2004168709 A | 6/2004 |
| JP | 2008536866 A | 9/2008 |
| JP | 2010514517 A | 5/2010 |
| JP | 2012508793 A | 4/2012 |
| WO | WO-9612711 A1 | 5/1996 |
| WO | WO-0006135 A2 | 2/2000 |
| WO | WO-02080915 A2 | 10/2002 |
| WO | WO-02100437 A2 | 12/2002 |
| WO | WO-2007011874 A2 | 1/2007 |
| WO | WO-2008083118 A1 | 7/2008 |
| WO | WO-2009015286 A2 | 1/2009 |
| WO | WO-2009077736 A2 | 6/2009 |
| WO | WO-2010070664 A1 | 6/2010 |
| WO | WO-2010125416 A1 | 11/2010 |
| WO | WO-2010135731 A1 | 11/2010 |
| WO | WO-2012119070 A2 | 9/2012 |
| WO | WO-2013041967 A2 | 3/2013 |
| WO | WO-2014161002 A2 | 10/2014 |
| WO | WO-2015031186 A1 | 3/2015 |
| WO | WO-2015031187 A1 | 3/2015 |
| WO | WO-2015094392 A1 | 6/2015 |
| WO | WO-2016205068 A1 | 12/2016 |
| WO | WO-2016205069 A1 | 12/2016 |
| WO | WO-2016205071 A1 | 12/2016 |
| WO | WO-2017053646 A1 | 3/2017 |
| WO | WO-2017160548 A1 | 9/2017 |
| WO | WO-2019135927 A1 | 7/2019 |
| WO | WO-2020076769 A1 | 4/2020 |
| WO | WO-2020117637 A1 | 6/2020 |
| WO | WO-2020219707 A1 | 10/2020 |
| WO | WO-2022081204 A1 | 4/2022 |
| WO | WO-2022232205 A1 | 11/2022 |
| WO | WO-2023091439 A1 | 5/2023 |
| WO | WO-2023114347 A1 | 6/2023 |

OTHER PUBLICATIONS

Chung et al., The effect of dioptric blur on reading performance. Vision Res 47(12):1584-94 (2007).
Co-pending U.S. Appl. No. 18/239,045, inventor Horn; Gerald, filed on Aug. 28, 2023.
Co-pending U.S. Appl. No. 18/239,072, inventor Horn; Gerald, filed on Aug. 28, 2023.
Co-pending U.S. Appl. No. 18/239,087, inventor Horn; Gerald, filed on Aug. 28, 2023.
Co-pending U.S. Appl. No. 18/241,733, inventor Horn; Gerald, filed on Sep. 1, 2023.
Co-pending U.S. Appl. No. 18/369,737, inventor Horn; Gerald, filed on Sep. 18, 2023.
Co-pending U.S. Appl. No. 18/465,918, inventor Horn; Gerald, filed on Sep. 12, 2023.
Cowan et al., Clinical evaluation of a new mydriatic-mydrilate. Br J Ophthalmol 46(12):730-6 (1962).
Davidson., General medicine and visual side effects. Br Med J 1(6166):821 (1979).
Drance et al., Dose response of human intraocular pressure to aceclidine. Arch Ophthalmol 88(4):394-6 (1972).
Edwards., Behaviour of the fellow eye in acute angle-closure glaucoma. Br J Ophthalmol 66(9):576-9 (1982).
Edwards et al., Effect of brimonidine tartrate 0.15% on night-vision difficulty and contrast testing after refractive surgery, J Cataract Refract Surg. 34(9):1538-41 (2008).
Ehlert et al. The interaction of the enantiomers of aceclidine with subtypes of the muscarinic receptor. J Pharmacol Exp Ther 279(3):1335-1344 (1996).
Fechner et al., Accomodative effects of aceclidine in the treatment of glaucoma. Amer J Ophth. 79 (1):104-106 (1975).
Francois et al. Ultrasonographic study of the effect of different miotics on the eye components. Ophthalmologica 175(6):328-338 (1977).
Fricke et al. Global Prevalence of Presbyopia and Vision Impairment from Uncorrected Presbyopia: Systematic Review, Meta-analysis, and Modelling. Ophthalmology 125(10):1492-1499 (2018).
Gardiner., ABC of Ophthalmology: accidents and first aid. Br Med J 2(6148):1347-50 (1978).

(56) References Cited

OTHER PUBLICATIONS

Gardiner., ABC of Ophthalmology: Methods of examination. Br Med J 2(6152):1622-6 (1978).
Glaucadrine, poudre et solvant pour collyre en solution, boite de 1 acon de lyophilisat + acon le solvant de 10 ml GI. Available at Http://www.doctissimo.fr/medicament-GLAUCADRINE.htm Machine Translation Provided. 2018.
GLAUNORM toma all'INDICE farmaci. Available at http://www.anibaldi.eu/farmaci/schedetecniche/GLAUNORM.html. (last updated Dec. 15, 2012) Machine Translation Provided.
Grünberger et al., The pupillary response test as a method to differentiate various types of dementia. Neuropsychiatr 23(1):52-57 (2009).
Hoyng et al., The combination of guanethidine 3% and adrenaline 0.5% in 1 eyedrop (GA) in glaucoma treatment. Br J Ophthalmol 63(1):56-62 (1979).
Ishikawa et al. Selectivity of muscarinic agonists including (+/-)-aceclidine and antimuscarinics on the human intraocular muscles. J Ocul Pharmacol Ther 14(4):363-373 (1998).
Josefa Valcarcel, Glaucostat(R) 2% colirio. Machine Translation Provided. 2000.
Kaufman et al. Presbyopia and Glaucoma: Two Diseases, One Pathophysiology? The 2017 Friedenwald Lecture. Invest Ophthalmol Vis Sci 60(5):1801-1812 (2019).
KIBBE. Handbook of Pharmaceutical Excipients. 3rd Edition, American Pharmaceutical Association and Pharmaceutical Press (pp. 416-419) (2000).
Latanoprost Label (2006).
Lubrizol Pharmaceutical Bulletin 21 (Lubrizol Advanced Materials, Inc.) May 31, 2011.
Mayama et al. Myopia and advanced-stage open-angle glaucoma. Ophthalmology 109(11):2072-2077 (2002).
MAYO Clinic: Tropicamide (Opthalmic Route), 2015, http://www.mayoclinic.org/drugs-supplements/tropicamide-ophthalmic-route/description/drg-20066481.
Mohan et al., Optimal dosage of cyclopentolate 1% for cycloplegic refraction in hypermetropes with brown irides. Indian J Ophthalmol 59(6):514-6 (2011).
Muller and R.P. Dessing (Eds.) 4th Edition, European Drug Index, European Society of Clinical Pharmacy, Jeutscher Apotheker Verlag Suttgart (p. 550) (1997).
Nayak et al., A comparison of cycloplegic and manifest refractions on the NR-1000F (an objective Auto Refractometer). Br J Ophthalmol 71(1):73-5 (1987).
PARK., The comparison of mydriatic effect between two drugs of different mechanism. Korean J Ophthalmol 23(1):40-2 (2009).
PCT/US2014/052256 International Search Report and Written Opinion dated Dec. 18, 2014.
PCT/US2016/036687 International Search Report and Written Opinion dated Sep. 9, 2016.
PCT/US2016/036692 International Search Report and Written Opinion dated Sep. 22, 2016.
PCT/US2016/036694 International Search Report and Written Opinion dated Oct. 26, 2016.
PCT/US2017/021244 International Search Report and Written Opinion dated May 22, 2017.
PCT/US2019/055116 International Search Report and Written Opinion dated Dec. 19, 2019.
PCT/US2019/063923 International Invitation to Pay Additional Fees dated Feb. 3, 2020.
PCT/US2019/063923 International Search Report and Written Opinion dated Apr. 23, 2020.
PCT/US2021/029536 International Search Report and Written Opinion dated Aug. 9, 2021.
PCT/US2022/026435 International Invitation to Pay Additional Fees dated Jul. 5, 2022.
PCT/US2022/026435 International Search Report and Written Opinion dated Sep. 28, 2022.
Prospectus/Technical Sheet for Glaucostat Josefa Valcarecel GLAUCOSTAT® 2% colirio (2000).
PubChem 233021624 deposited on Feb. 12, 2015 (Feb. 12, 2015).
PubChem-CID-22416839, Create Date: Dec. 5, 2007.
ROMANO., Double-blind cross-over comparison of aceclidine and pilocarpine in open-angle glaucoma. Br J Ophthalmol 54(8):510-21 (1970).
Smith et al., Subsensitivity to cholinoceptor stimulation of the human iris sphincter in situ following acute and chronic administration of cholinomimetic miotic drugs. Br J Pharmacol 69(3):513-8 (1980).
STELLA. Prodrugs: Some Thoughts and Current Issues. J Pharm Sci 99(12):4755-4765 (2010).
Tataru et al., Antiglaucoma pharmacotherapy. J Med Life 5(3):247-51 (2012).
Trinavarat et al., Effective pupil dilatation with a mixture of 0.75% tropicamide and 2.5% phenylephrine: A randomized controlled trial. Indian J Ophthalmol 57(5):351-4 (2009).
U.S. Appl. No. 14/223,639 Office Action dated Jan. 5, 2015.
U.S. Appl. No. 14/223,639 Office Action dated Sep. 30, 2014.
U.S. Appl. No. 14/742,903 Office Action dated Dec. 2, 2015.
U.S. Appl. No. 14/742,903 Office Action dated Jul. 17, 2015.
U.S. Appl. No. 14/742,921 Office Action dated Jul. 15, 2015.
U.S. Appl. No. 14/860,770 Office Action dated Dec. 13, 2016.
U.S. Appl. No. 14/860,777 Office Action dated Mar. 9, 2017.
U.S. Appl. No. 15/073,089 Office Action dated May 8, 2017.
U.S. Appl. No. 15/073,089 Office Action dated Nov. 30, 2016.
U.S. Serial No. 15/073,139 Office Action dated Dec. 1, 2016.
U.S. Appl. No. 15/235,431 Office Action dated Mar. 9, 2018.
U.S. Appl. No. 15/864,703 Office Action dated Apr. 8, 2019.
U.S. Appl. No. 15/864,703 Office Action dated Feb. 11, 2019.
U.S. Appl. No. 15/864,703 Office Action dated Mar. 26, 2018.
U.S. Appl. No. 15/956,931 Office Action dated Oct. 2, 2018.
U.S. Appl. No. 15/956,936 Office Action dated Feb. 11, 2019.
U.S. Appl. No. 15/956,936 Office Action dated Sep. 28, 2018.
U.S. Appl. No. 16/106,730 Office Action dated Jun. 11, 2021.
U.S. Appl. No. 16/106,730 Office Action dated Jun. 2, 2020.
U.S. Appl. No. 16/106,730 Office Action dated Oct. 19, 2020.
U.S. Appl. No. 16/156,276 Office Action dated Jun. 26, 2020.
U.S. Appl. No. 16/156,276 Office Action dated Oct. 22, 2020.
U.S. Appl. No. 16/700,088 Office Action dated May 28, 2021.
U.S. Appl. No. 16/700,088 Office Action dated Nov. 2, 2021.
U.S. Appl. No. 16/747,070 Office Action dated Jun. 25, 2021.
U.S. Appl. No. 16/747,070 Office Action dated Oct. 30, 2020.
U.S. Appl. No. 16/796,364 Office Action dated Apr. 30, 2021.
U.S. Appl. No. 16/796,364 Office Action dated Dec. 30, 2020.
U.S. Appl. No. 16/796,364 Office Action dated Jun. 11, 2021.
U.S. Appl. No. 16/881,570 Office Action dated Oct. 7, 2020.
U.S. Appl. No. 17/069,155 Office Action dated Aug. 19, 2021.
U.S. Appl. No. 17/242,398 Office Action dated Apr. 27, 2023.
U.S. Appl. No. 17/242,398 Office Action dated Oct. 14, 2022.
U.S. Appl. No. 17/502,066 Office Action dated Jun. 22, 2023.
U.S. Appl. No. 17/502,066 Office Action dated Mar. 31, 2022.
U.S. Appl. No. 17/502,066 Office Action dated Nov. 14, 2022.
U.S. Appl. No. 17/552,622 Office Action dated Feb. 9, 2023.
U.S. Appl. No. 17/552,654 Office Action dated Apr. 20, 2022.
U.S. Appl. No. 17/552,654 Office Action dated Dec. 2, 2022.
U.S. Appl. No. 18/239,072 Office Action dated Nov. 21, 2023.
U.S. Appl. No. 18/239,087 Office Action dated Oct. 10, 2023.
Varma et al. Concentration of Latanoprost Ophthalmic Solution after 4 to 6 Weeks' Use in an Eye Clinic Setting. Invest Ophthalmol Vis Sci. 47(1):222-225 (2006).
Ward et al., 1,2,5-Thiadiazole analogues of aceclidine as potent ml muscarinic agonists. J Med Chem 41(3):379-392 (1988).
Wood et al., Pupil dilatation does affect some aspects of daytime driving performance. Br J Ophthalmol (11):1387-90 (2003).
Zhang et al. Reactive impurities in large and small molecule pharmaceutical excipients—A review. TrAC Trends in Analytical Chemistry 101:34-42 (2018).
Co-pending U.S. Appl. No. 18/606,475, inventor Horn; Gerald, filed on Mar. 15, 2024.
Co-pending U.S. Appl. No. 18/606,489, inventor Horn; Gerald, filed on Mar. 15, 2024.
Co-pending U.S. Appl. No. 18/606,509, inventor Horn; Gerald, filed on Mar. 15, 2024.

(56) References Cited

OTHER PUBLICATIONS

Jiao, Polyoxyethylated nonionic surfactants and their applications in topical ocular drug delivery, Advanced Drug Delivery Reviewed 60 (2008) 1663-1673 (Year: 2008).
U.S. Appl. No. 17/502,066 Office Action dated Mar. 27, 2024.
U.S. Appl. No. 18/239,072 Office Action dated Mar. 27, 2024.
Barot et al. Prodrug Strategies. Ocular Drug Delivery Med. Chem. 8(4):753-768 (2012).
DIAMONDS- BCdVA and Refraction Guideline, Version 1.0, Jan. 12, 2016, 10 pages.
Krise et al. A novel prodrug approach for tertiary amines. 2. Physicochemical and in vitro enzymatic evaluation of selected N-phosphonooxymethyl prodrugs. J Pham Sci 88(9):922-927 (1999).
Mäntylä et al. Design, synthesis and in vitro evaluation of novel water-soluble prodrugs of buparvaquone. Eur J Pharm Sci 23(2):151-158 (2004).
Pramanik et al. A new route to cevimeline. Tetrahedron Letters 54(24):3043-3045 (2013).
PubChem CID-22416839, Dec. 5, 2007.
U.S. Appl. No. 18/239,045 Office Action dated Jan. 26, 2024.
U.S. Appl. No. 18/239,087 Office Action dated Jan. 25, 2024.
U.S. Appl. No. 18/241,733 Office Action dated Jan. 30, 2024.
U.S. Appl. No. 18/465,918 Office Action dated Feb. 1, 2024.
Aceclidine (Hydrochloride) Item No. 1790. Product Information. Cayman Chemical Company (1 pg) (Dec. 2, 2022).
Charman, W. Neil. Pinholes and presbyopia: solution or sideshow? Ophthalmic Physiol Opt 39(1):1-10 (2019).
Co-pending U.S. Appl. No. 18/763,722, inventors Horn; Gerald et al., filed on Jul. 3, 2024.
Co-pending U.S. Appl. No. 18/765,066, inventors Horn; Gerald et al., filed on Jul. 5, 2024.
Co-pending U.S. Appl. No. 18/765,156, inventors Horn; Gerald et al., filed on Jul. 5, 2024.
Co-pending U.S. Appl. No. 18/766,429, inventors Horn; Gerald et al., filed on Jul. 8, 2024.
Drug information Q&A "Q29". What is the expiry date of drugs and how to store them properly?, Japan Pharmaceutical Manufacturers Association [online], Mar. 2014, [retrieved on Mar. 25, 2024], Retrieved from the Internet: URL: https://www.jpma.or.jp/about_medicine/guide/med_qa/q29.html (English translation provided).
Randazzo et al., Pharmacological management of night vision disturbances after refractive surgery Results of a randomized clinical trial. J Cataract Refract Surg 31(9):1764-1772 (2005).
Santvliet, et al. Determinants of Eye Drop Size. Survey of Ophthamology 49(2):197-213 (2004).
U.S. Appl. No. 17/730,376 Office Action dated Jul. 17, 2024.
U.S. Appl. No. 18/369,737 Office Action dated Jun. 6, 2024.
Xu, Renfeng et al. Effect of Target Luminance on Optimum Pupil Diameter for Presbyopic Eyes. Optom Vis Sci 93(11):1409-1419 (2016).

\* cited by examiner

ACECLIDINE DERIVATIVES, COMPOSITIONS THEREOF AND METHODS OF USE THEREOF

BACKGROUND OF THE INVENTION

Aceclidine is a muscarinic agonist with a quinuclidine ring (a tertiary nitrogen as part of a heterocyclic carbon ring) along with an acetyl ester bond to the heterocyclic ring two carbons away. In some cases, stability in solution is problematic for aceclidine. The need to reconstitute aceclidine where stability in solution is an issue adds undesirable complexity in terms of patient compliance, adherence to sterile technique, which becomes essentially impossible, as well as other possible reformulation errors. For example, aceclidine has been commercially available for treatment of glaucoma as the salt, aceclidine HCl, for over forty years. During that time it has only been available as a lyophilized powder to be reconstituted by the user at the time of use.

In addition to its potential use as a glaucoma agent as in past years, aceclidine may have other applications as well, particularly for intraocular use, such as the treatment of presbyopia. Presbyopia is a normal and inevitable effect of ageing and is the first unmistakable sign for many in their forties that they are getting older. One study found that more than 1 billion people worldwide were presbyopic in 2005. This same study predicted that number to almost double by the year 2050. If everyone over the age of 45 is considered to be presbyopic, then an estimated 122 million people in the United States alone had presbyopia in 2010. As baby boomers reach the critical age, this number is only going to increase.

Presbyopia carries with it a stigma resulting from the limitation in ability to quickly function at many tasks requiring focusing at both distant and near points, which once occurred almost immediately. In the presbyopic patient, these tasks can be performed only by the use of eyeglasses, contact lenses or after undergoing invasive surgery. One such optical modification, the monovision procedure, can be executed with the use of glasses, contact lenses or even surgery. The monovision procedure corrects one eye for near focus and the other eye for distance focus. However, monovision correction is normally accompanied by loss of depth perception and distance vision particularly in dim light (e.g. night). Other surgical procedures that have been developed to relieve presbyopia include: (1) the implantation of intraocular lenses (INTRACOR®; registered trademark of Technolas Perfect Vision GMBH); (2) reshaping of the cornea (PresbyLASIK and conductive keratoplasty); (3) scleral band expansion; and (4) implantation of corneal inlays (Flexivue Microlens®; registered trademark of PresbiBio LLC, Kamra®; registered trademark of AcuFocus, Inc. and Vue+). Kamra® corneal inlays manufactured by AcuFocus work by inlaying a pinhole on the cornea to increase the depth of focus. A similar effect can be achieved with general miotic agents, such as pilocarpine (a non-selective muscarinic acetylcholine receptor agonist), carbachol (a non-selective muscarinic acetylcholine receptor agonist), and phospholine iodide (an acetylcholinesterase inhibitor). These general miotic agents trigger increased ciliary muscle contraction and induce accommodation of any remaining reserves, improving near vision at the expense of distance vision in individuals who still retain some accommodative function. While these general miotic agents also create improved depth of focus via a pinhole effect induced by pupillary miosis (i.e. constriction), to the degree accommodation occurs, the pinhole effect only partially offsets the induced accommodative myopia for distance. In some cases, such as with pilocarpine or carbachol, the induced accommodation may create up to 5 diopters or more of induced myopia resulting in induced myopia causing blurred distance vision generally and during shift of the focal point from distance to near. These general miotic agents also cause substantial redness, severe nasal congestion and create ciliary muscle spasms, which commonly induces discomfort that can be severe and long-lasting. In extreme cases, such ciliary muscle spasms can result in retinal detachment.

Aceclidine provides enhanced presbyopic reversal while causing little to no side effects. However, aceclidine, like many quinuclidine-ring containing muscarinic agonists has a poor shelf-life and is difficult to solubilize. Thus, there is a need in the art for stable solubilized forms of aceclidine.

SUMMARY OF THE INVENTION

The present invention provides derivatives of aceclidine.

In another embodiment, the present invention provides an ophthalmological composition comprising a therapeutically effective amount of a compound of the present invention and one or more pharmaceutically acceptable excipients.

In another embodiment, the present invention provides an ophthalmological composition comprising a therapeutically effective amount of a compound of the present invention wherein the pH of the composition is at least 3 log units less than the pKa of the compound.

In another embodiment, the present invention provides an ophthalmological composition comprising a therapeutically effective amount of a compound of the present invention and a cyclodextrin wherein the pH of the composition is at least 3 log units less than the pKa of the compound.

In another embodiment, the present invention provides an ophthalmological composition comprising a therapeutically effective amount of a compound of the present invention and a cyclodextrin selected from an alpha-cyclodextrin, a beta-cyclodextrin and a gamma-cyclodextrin wherein the pH of the composition is at least 3 log units less than the pKa of the compound.

In another embodiment, the present invention provides a method of treating presbyopia or glaucoma comprising administering to a patient in need thereof a therapeutically effective amount of a compound of the present invention.

In another embodiment, the present invention provides a method of reducing hyperemia comprising administering to a patient in need thereof a therapeutically effective amount of a compound of the present invention.

In one embodiment, the present invention provides a compound of formula (I)

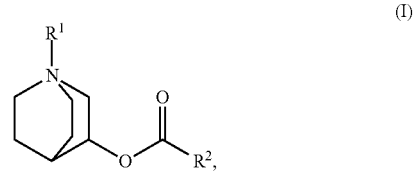

wherein $R^1$ is absent or an alkyl wherein when $R^1$ is absent the adjacent nitrogen is positively charged, and wherein $R^2$ is an amine or tert-butyl, or any pharmaceutically acceptable salt, ester or prodrug thereof.

In a preferred embodiment, the present invention provides a compound of formula (II)

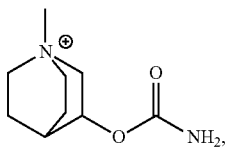

(II)

or any pharmaceutically acceptable salt, ester or prodrug thereof.

In another preferred embodiment, the present invention provides a compound of formula (III)

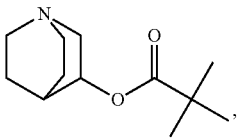

(III)

or any pharmaceutically acceptable salt, ester or prodrug thereof.

DETAILED DESCRIPTION OF THE INVENTION

The present invention discovers aceclidine derivatives and compositions thereof that are more stable than aceclidine hydrochloride.

In one embodiment, the present invention provides a compound of formula (I)

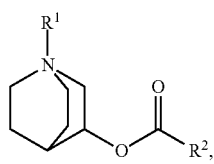

(I)

wherein $R^1$ is absent or an alkyl wherein when $R^1$ is absent the adjacent nitrogen is positively charged, and wherein $R^2$ is an amine or tert-butyl, or any pharmaceutically acceptable salt, ester or prodrug thereof.

In a preferred embodiment, the present invention provides a compound of formula (II)

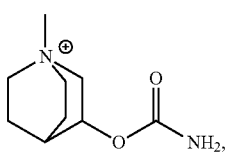

(II)

or any pharmaceutically acceptable salt, ester or prodrug thereof.

In another preferred embodiment, the present invention provides a compound of formula (III)

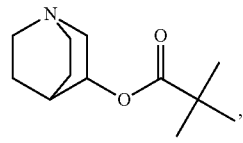

(III)

or any pharmaceutically acceptable salt, ester or prodrug thereof.

Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used herein, the term "composition" is intended to encompass a product comprising the specified ingredients in the specified amounts, as well as any product which results, directly or indirectly, from a combination of the specified ingredients in the specified amounts.

The terms "treating" and "treatment" refer to reversing, alleviating, inhibiting, or slowing the progress of the disease, disorder, or condition to which such terms apply, or one or more symptoms of such disease, disorder, or condition.

As used herein, the term "effective amount" refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, an "effective amount" will depend upon the context in which it is being administered. An effective amount may be administered in one or more prophylactic or therapeutic administrations.

As used herein, the term "pharmaceutically acceptable" describes a material that is not biologically or otherwise undesirable, i.e., without causing an unacceptable level of undesirable biological effects or interacting in a deleterious manner.

As used herein the term "patient" refers but is not limited to a person or other animal.

As used herein, the term $R^1$ refers to an alkyl.

As used herein, the term $R^2$ refers to an amine or a tert-butyl.

As used herein, term "alkyl" is a branched or straight-chain alkyl consisting of a saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or straight-chained. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, thiol, a phosphate or a sulfate.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as 2H, 3H, 13 C, 14 C, 15 N, 18 O, 17 O, 35 S, 18F and 36 Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as 3H and 14 C are incorporated, are useful in drug and/or substrate tissue distribution assays. Tritiated, i.e., 3H, and carbon-14, i.e., 14 C, isotopes are particularly preferred for their ease of preparation and detectability. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

The term "prodrug" or "prodrugs" refers to compounds, including monomers and dimers of the compounds of the invention, which have cleavable groups and become under physiological conditions compounds which are pharmaceutically active in vivo.

As used herein "ester" or "esters" is represented by the formula —OC(O)$A^1$ or —C(O)O$A^1$, where $A^1$ can be alkyl, cycloalkyl, alkenyl, cycloalkenyl, alkynyl, cycloalkynyl, aryl, a heteroaryl group or other suitable substituent.

As used herein "salt" or "salts" refers to those salts which retain the biological effectiveness and properties of the parent compounds and which are not biologically or otherwise harmful at the dosage administered. Salts of the compounds of the present inventions may be prepared from inorganic or organic acids or bases.

The compounds of the present invention can be used in the form of pharmaceutically acceptable salts derived from inorganic or organic acids or bases. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq.

The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, malic acid, sulphuric acid and phosphoric acid and such organic acids as oxalic acid, malic acid, maleic acid, methanosulfonic acid, succinic acid and citric acid. Preferred acid addition salts are prepared from methanosulfonic acid, malic acid and phosphoric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Compounds of the Invention

In a preferred embodiment, aceclidine derivatives of the present invention include:

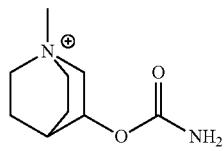

and

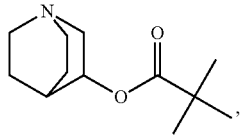

or any pharmaceutically acceptable salt, ester or prodrug thereof.

Methods of making the compounds of the present invention are within the skill of a person skilled in the relevant art.

Compositions of the Invention

Compositions of the present invention include excipients not limited to surfactants, viscosity enhancers, tonicity adjustors, osmolality modifiers, solubility enhancers, preservatives and buffers.

Surfactants suitable for the present invention include, but are not limited to, nonionic, cationic and/or anionic surfactants. Specific surfactants include cyclodextrins, polyoxyl alkyls, poloxamers or combinations thereof. Further, substitution of other surfactants compatible with ophthalmic use allows for similar composition advantages, which may included but is not limited to one or more of a nonionizing surfactant such as poloxamer, Poloxamer 188, Poloxamer 407, Polysorbate 20, Polysorbate 80, ionically charged (e.g. anionic) beta-cyclodextrins with or without a butyrated salt (Captisol®; (sulfobutylether β-cyclodextrin, Captisol is a registered trademark of Cydex Pharmaceuticals), 2-hydroxypropyl beta cyclodextrin ("HPβCD"), Polyoxyl 35 stearate, Polyoxyl 40 castor oil and Polyoxyl 40 hydrogenated castor oil, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxol, polyoxyl stearate, nonoxynol, octyphenol ethoxylates, nonyl phenol ethoxylates, capryols, lauroglycol, PEG such as PEG400, Brij® 35 (polyoxyethyleneglycol dodecyl ether; Brij is a registered trademark of Uniqema Americas LLC), glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis(2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N'-bis(2-hydroxypropane sulfonic acid) (POPSO), N-tris(hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl)methyl-2-aminoethane sulfonic acid (TES), 2-Amino-2-hydroxymethyl-propane-1,3-diol (Tris), tyloxapol, Span® 20-80 (sorbitan monolaurate, sorbitan monopalmitate, sorbitan monostearate, and sorbitan monooleate; Span is a registered trademark of Uniqema Americas Inc.), Tween® 20 (Tween is a registered trademark of Uniqema Americas LLC), Tween® 80, Labrasol® (caprylocaproyl macrogol-8 glycerides; Labrasol is a registered trademark of Gattefosse SAS). Surfactants of the present invention can be at a concentration from about 0.01% to about 99% w/v, preferably from about 1% to about 30% w/v.

Solubility enhancers (i.e. solvents) suitable for the present invention include, but are not limited to, glycofurol (a.k.a. tetraglycol and tetraethylene glycol), dimethyl sulfoxide ("DMSO"), vitamin E TPGS (d-alpha tocopheryl polyethylene glycol 1000 succinate), dimethyl sorbide ("DMI"), ethyl acetate, acetonitrile, ethyl alcohol, alcohols, polyols, amides, esters, polyethylene glycol, propylene glycol, propylene glycol ethers, polysorbates, poloxamers, cyclodextrins, Span® 20-80, dimethyl isosorbide, isopropyl myristate oil and complexing agents such as cyclodextrins and nicotinamide or a combination thereof.

Viscosity enhancers suitable for the present invention include, but are not limited to, carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxyethyl cellulose, or hydroxyethyl cellulose, hyaluronic acid, dextran, polyethylene glycol, polyvinyl alcohol, polyvinyl pyrrolidone, gellan, carrageenan, alignic acid, carboxyvinyl polymer or combinations thereof.

A tonicity adjustor can be, without limitation, a salt such as sodium chloride ("NaCl"), potassium chloride, mannitol or glycerin, or another pharmaceutically or ophthalmically acceptable tonicity adjustor. In certain embodiments the tonicity adjustor is 0.3% w/v glycerin. In other embodiments the tonicity adjustor is 0.037% w/v NaCl.

Glycofurol is formulated in the topical compositions of the present invention due to its percutaneous absorption ability and its "generally recognized as safe" (GRAS) status in the Handbook of Pharmaceutical Excipients.

Osmolality modifiers suitable for the present invention include, but are not limited to, mannitol, sorbitol, glycerol and a combination thereof.

Preservatives that can be used with the present invention include, but are not limited to, benzalkonium chloride (BAK), chlorobutanol, thimerosal, phenylmercuric acetate, disodium ethylenediaminetetraacetic acid, phenylmercuric nitrate, perborate or benzyl alcohol. In a preferred embodiment the preservative is BAK at a concentration of about 0.001% to about 1.0% w/v, more preferably at a concentration of about 0.02% w/v.

Various buffers and means for adjusting pH can be used to prepare ophthalmological compositions of the invention. Such buffers include, but are not limited to, acetate buffers, citrate buffers, citric acid buffers, phosphate buffers and borate buffers. It is understood that acids or bases can be used to adjust the pH of the composition as needed, preferably of 1 to 10 mM concentration, and more preferably about 5 mM. In a preferred embodiment the pH is from about 4.0 to about 8.0, in a more preferred embodiment the pH is from about 7.0 to about 7.5 in a most preferred embodiment the pH is about 5.0 or 7.4.

In a more preferred embodiment, the present invention includes storing compounds of the invention at a pH of at least 3 log units lower than the pKa of the compound.

In an even more preferred embodiment, the present invention includes the addition of an alpha, beta or gamma-cyclodextrin to further enhance stability. Not wishing to be held to a particular theory, the selection of the most preferred cyclodextrin is dependent upon the size of the drug/prodrug in proportion to the nonpolar cavity of the cyclodextrin.

What is claimed is:

1. A pharmaceutically acceptable salt of a compound comprising a cation of formula (I),

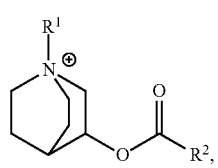

(I)

wherein $R^1$ is an alkyl, and wherein $R^2$ is an amine or tert-butyl.

2. An ophthalmological composition comprising a therapeutically effective amount of (i) a pharmaceutically acceptable salt of a compound comprising a cation of formula (I):

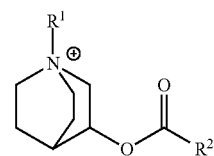

(I)

wherein $R^1$ is an alkyl, and wherein $R^2$ is an amine or tert-butyl, or (ii) a compound of formula (III)

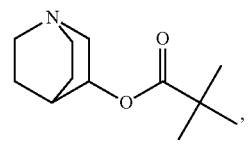

(III)

or a pharmaceutically acceptable salt thereof, wherein the pH of the composition is at least 3 log units less than the pKa of the compound.

3. The composition of claim 2, further comprising a cyclodextrin.

4. The composition of claim 3, wherein the cyclodextrin is selected from an alpha-cyclodextrin, a beta-cyclodextrin and a gamma-cyclodextrin.

5. A method of treating presbyopia or glaucoma comprising administering to a patient in need thereof a therapeutically effective amount of (i) a pharmaceutically acceptable salt of a compound comprising a cation of formula (I):

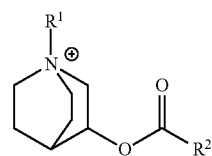

(I)

wherein $R^1$ is an alkyl, and wherein $R^2$ is an amine or tert-butyl, or (ii) a compound of formula (III)

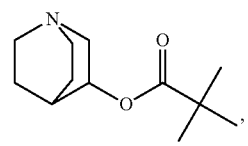

(III)

or a pharmaceutically acceptable salt thereof.

6. A method of reducing hyperemia comprising administering to a patient in need thereof a therapeutically effective amount of (i) a pharmaceutically acceptable salt of a compound comprising a cation of formula (I):
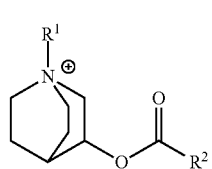
(I)
wherein $R^1$ is an alkyl, and
wherein $R^2$ is an amine or tert-butyl, or
(ii) a compound of formula (III)
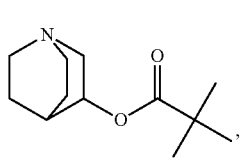
(III)
or a pharmaceutically acceptable salt thereof.
* * * * *